United States Patent
Schmitt et al.

(10) Patent No.: US 10,508,973 B2
(45) Date of Patent: Dec. 17, 2019

(54) METHOD FOR DETERMINING THE REFRACTIVE INDEX PROFILE OF A CYLINDRICAL OPTICAL OBJECT, PARTICULARLY A PREFORM FOR AN OPTICAL FIBER

(71) Applicant: Heraeus Quarzglas GmbH & Co. KG, Hanau (DE)

(72) Inventors: Maximilian Schmitt, Dieburg (DE); Bodo Kühn, Gelnhausen (DE)

(73) Assignee: Heraeus Quarzglas GmbH & Co. KG, Hanau (DE)

(*) Notice: Subject to any disclaimer, the term of this patent is extended or adjusted under 35 U.S.C. 154(b) by 0 days.

(21) Appl. No.: 15/785,690

(22) Filed: Oct. 17, 2017

(65) Prior Publication Data
US 2018/0113052 A1  Apr. 26, 2018

(30) Foreign Application Priority Data
Oct. 26, 2016  (EP) .................................... 16195864

(51) Int. Cl.
*G01M 11/00* (2006.01)
*G01M 11/02* (2006.01)
(Continued)

(52) U.S. Cl.
CPC ........ *G01M 11/35* (2013.01); *G01M 11/0228* (2013.01); *G01M 11/37* (2013.01); *G01N 21/412* (2013.01); *G02B 6/0365* (2013.01)

(58) Field of Classification Search
CPC .. G01M 11/35; G01M 11/0228; G01M 11/37; G02B 6/0365; G02B 6/0288;
(Continued)

(56) References Cited

U.S. PATENT DOCUMENTS 3,636,360 A * 1/1972 Oishi .................. G01F 23/2921
250/577
3,751,672 A * 8/1973 Michel ................ G01N 21/431
250/552
(Continued)

OTHER PUBLICATIONS https://en.wikipedia.org/wiki/Linear_regression.*
(Continued)

*Primary Examiner* — Mohamed K Amara
(74) *Attorney, Agent, or Firm* — Panitch Schwarze Belisario & Nadel LLP

(57) ABSTRACT

A method for determining the refractive index profile of a preform is provided. The method involves: preparing the measured deflection angle distribution, including an extreme value determination of the deflection angle distribution, to obtain a prepared deflection angle distribution; transforming the prepared deflection angle distribution into a prepared refractive-index profile; evaluating the prepared refractive-index profile for the fixation of orientation values for the layer radius and for the layer refractive index of a hypothetical refractive index profile; generating a simulated deflection angle distribution on the basis of the hypothetical refractive-index profile with the orientation values, and transforming the deflection angle distribution into a simulated refractive-index profile; fitting the simulated refractive index profile to the prepared refractive-index profile by iterative adaptation of parameters to obtain a fitted, simulated refractive-index profile which is defined by adapted parameters, and obtaining the refractive index profile as the hypothetical refractive-index profile with the adapted parameters.

13 Claims, 3 Drawing Sheets

(51) Int. Cl.
*G01N 21/41* (2006.01)
*G02B 6/036* (2006.01)

(58) Field of Classification Search
CPC .......... G01N 21/412; G01N 2021/0342; C03B 2203/22; C03B 2203/23; C03B 2203/26
See application file for complete search history.

(56) References Cited

U.S. PATENT DOCUMENTS

| | | | | |
|---|---|---|---|---|
| 4,181,433 A * | 1/1980 | Marcuse | ............... | G01N 21/412 356/128 |
| 4,227,806 A | 10/1980 | Watkins | | |
| 4,441,811 A | 4/1984 | Melezoglu et al. | | |
| 4,492,463 A * | 1/1985 | Marcuse | ............... | G01N 21/412 356/239.2 |
| 4,515,475 A | 5/1985 | Payne et al. | | |
| 4,519,704 A * | 5/1985 | Mansfield | ............ | G01N 21/412 356/128 |
| 4,726,677 A * | 2/1988 | Glantschnig | ......... | G01N 21/412 356/128 |
| 4,744,654 A | 5/1988 | Jinno et al. | | |
| 4,934,818 A * | 6/1990 | Glantschnig | ......... | G01N 21/412 356/128 |
| 5,078,488 A | 1/1992 | Yamaguchi et al. | | |
| 5,118,954 A * | 6/1992 | Grosso | ................ | G01B 11/105 250/559.24 |
| 5,365,329 A * | 11/1994 | Svendsen | ............... | G01M 11/37 356/128 |
| 5,396,323 A * | 3/1995 | Abbott, III | ............. | G01M 11/37 356/73.1 |
| 5,450,192 A * | 9/1995 | Nolf | ....................... | G01M 11/37 356/244 |
| 5,844,669 A * | 12/1998 | Wang | ....................... | B29C 70/54 356/72 |
| 6,131,414 A * | 10/2000 | Shimizu | ............... | C03B 37/0124 65/378 |
| 6,538,755 B1 | 3/2003 | Propst, Jr. | ............. | C03B 37/018 356/635 |
| 6,611,321 B1 * | 8/2003 | Sasaki | ................... | G01N 21/412 356/73.1 |
| 6,919,954 B2 * | 7/2005 | Sasaki | ................... | G01M 11/088 356/128 |
| 7,078,719 B2 * | 7/2006 | Pirinoli | ................ | G01B 11/046 250/559.36 |
| 7,317,856 B2 * | 1/2008 | Hirano | ............... | C03B 37/01228 385/123 |
| 7,880,898 B2 * | 2/2011 | Jeannot | ................. | G01B 11/08 356/601 |
| 8,013,985 B2 | 9/2011 | Cook | | |
| 8,322,166 B2 * | 12/2012 | Bookbinder | ........ | C03B 37/0253 65/378 |
| 8,786,863 B2 * | 7/2014 | Kato | ................... | G01M 11/0271 356/515 |
| 9,481,599 B2 * | 11/2016 | Bickham | .............. | G02B 6/0288 |
| 9,952,033 B2 * | 4/2018 | Martini | ............... | G01B 11/043 |
| 9,989,458 B2 * | 6/2018 | Cook | ..................... | G01M 11/37 |
| 2004/0257506 A1 * | 12/2004 | Tashiro | ............. | G02F 1/133553 349/123 |
| 2005/0057746 A1 * | 3/2005 | Takahashi | ............. | G01B 11/26 356/139.07 |
| 2005/0126227 A1 * | 6/2005 | Collaro | ............... | C03B 37/0253 65/378 |
| 2008/0285926 A1 * | 11/2008 | Sahu | ..................... | C03B 37/014 385/123 |
| 2009/0147268 A1 * | 6/2009 | Groot | ................... | G01B 9/0209 356/511 |
| 2010/0149639 A1 * | 6/2010 | Kim | ...................... | G02B 5/124 359/530 |
| 2010/0245805 A1 | 9/2010 | Cook | | |
| 2012/0263793 A1 * | 10/2012 | Vitaliano | ............. | G01N 21/554 424/490 |
| 2013/0070462 A1 * | 3/2013 | Jin | .......................... | F21V 7/04 362/298 |
| 2013/0155394 A1 * | 6/2013 | Saito | ...................... | G01N 21/03 356/128 |
| 2015/0233703 A1 * | 8/2015 | Martini | ................ | G01B 11/043 356/28 |
| 2015/0332451 A1 * | 11/2015 | Amzaleg | ................ | G06T 7/001 382/149 |
| 2016/0123873 A1 * | 5/2016 | Cook | ..................... | G01M 11/37 356/73.1 |
| 2016/0141154 A1 * | 5/2016 | Kamata | ............ | H01J 37/32935 324/671 |

OTHER PUBLICATIONS

Extended Search Report dated May 12, 2017 in EP Application No. 16195864.0.

Fleming et al, "Nondestructive Measurement for Arbitrary RIP Distribution of Optical Fiber Preforms," Journal of Lightwave Technology, vol. 22, No. 2, pp. 478-486 (2004).

Hutsel & Gaylord, "Concurrent Three-Dimensional Characterizaion of the Refractive-Index and Residual-Stress Distributions in Optical Fibers," Applied Optics, vol. 51, No. 22, pp. 5442-5452 (2012).

* cited by examiner

METHOD FOR DETERMINING THE REFRACTIVE INDEX PROFILE OF A CYLINDRICAL OPTICAL OBJECT, PARTICULARLY A PREFORM FOR AN OPTICAL FIBER

BACKGROUND OF THE INVENTION

An embodiment of the present invention relates to a method for determining a radial refractive-index profile of a cylindrical optical object, particularly a preform for an optical fiber. The cylinder optical object comprises a cylinder longitudinal axis around which at least one layer k with a layer radius $r_k$ and with a layer refractive index $n_k$ extends radially symmetrically. A deflection angle distribution $\Psi(y)$ is measured and the refractive index profile is reconstructed therefrom on the basis of a model.

Such cylindrical optical objects are, for instance, fiber preforms, optical fibers, light guides, or cylinder lenses. One of the important properties of such objects is their refractive index and the spatial distribution thereof, particularly the radial refractive-index distribution, which will also be called "refractive index profile" hereinafter. For instance, the refractive index profile of the fiber preform defines the waveguide characteristics of the optical fiber drawn therefrom. The optical objects of relevance in this case have a homogeneous or a stepped refractive-index profile. These are particularly optical preforms with a step index profile in the case of which a core with a higher refractive index is surrounded by at least one cladding layer with a lower refractive index.

The refractive index distribution, however, cannot be measured directly. Therefore, it is normally determined indirectly as a deflection or interference of a light beam which is transmitted through a volume region of the optical element, the stepwise transmission being also called "scanning" hereinafter. The real cause, i.e. the spatial refractive-index distribution in the optical element, can be inferred from the interference or the deflection of the exiting light beam (exit beam) based on the beam direction at the beam entrance point (entry beam). The family of the deflection angles measured during scanning of the light beam in a direction transverse to the cylinder longitudinal axis (in y-direction) is herein also called "deflection angle distribution" $\Psi(y)$. For a better view and illustration, the geometric relationships are schematically shown in FIG. 3. The deflection angle $\Psi$ is defined as the angle between exit beam 33 and entry beam 32, and y is defined as the distance between the cylinder longitudinal axis L and the entry point E of the entry beam 32. For radially symmetric objects with a step index distribution of the refractive index, it can be described mathematically with reference to the following formula (1):

$$\Psi_m(x) = \begin{cases} 2 \cdot \sum_{k=1}^{m} \left[ \arcsin\left(\frac{y}{r_k} \cdot \frac{n_0}{n_{k-1}}\right) - \arcsin\left(\frac{y}{r_k} \cdot \frac{n_0}{n_k}\right) \right], & \text{for } r_{m+1} \cdot \frac{n_{m+1}}{n_0}, r_{m+1} \cdot \frac{n_m}{n_0} \le |y| < r_m \cdot \frac{n_m}{n_0} \\ 2 \cdot \sum_{k=1}^{m-1} \left[ \arcsin\left(\frac{y}{r_k} \cdot \frac{n_0}{n_{k1}}\right) - \arcsin\left(\frac{y}{r_k} \cdot \frac{n_0}{n_k}\right) \right] + \\ \quad 2 \cdot \arccos\left(\frac{y}{r_m} \cdot \frac{n_0}{n_{m1}}\right), & \text{for } r_{m+1} \cdot \frac{n_{m+1}}{n_0} \le |y| < r_{m+1} \cdot \frac{n_m}{n_0} \\ 0, & \text{for } |y| \ge r_1 \end{cases} \quad (1)$$

where:
m is the number of the layers of the object
$n_0$ is the refractive index of the surrounding medium
$n_k$ is the refractive index of the k-th layer
$r_k$ is the radius of the k-th layer A known mathematical method for calculating the refractive index profile from the "deflection angle distribution" $\Psi(y)$ based on measurement data according to equation (1) is based on the so-called "Abel transform".

$$n[r(y)] = n_0 \cdot \exp\left(\frac{1}{\pi} \cdot \int_y^R \frac{\Psi(t)dt}{\sqrt{t^2 - y^2}}\right) \quad (2)$$

where:
r shortest distance from the cylinder longitudinal axis of the object to the beam path, namely:

$$r(y) = y \cdot \exp\left(-\frac{1}{\pi} \cdot \int_y^R \frac{\Psi(t)dt}{\sqrt{t^2 - y^2}}\right) \quad (3)$$

R reference point for the refractive index distribution, namely the radial position of the reference refractive index (atmosphere or index liquid outside the object), and
$\Psi$ is substituted by $\delta\Phi/\delta t$ U.S. Pat. No. 4,227,806 describes a method for non-destructively determining parameters of an optical fiber preform. The preform is scanned by means of a laser beam entering transversely into the core-cladding structure, and the deflection angle of the exiting beam is measured and subsequently compared to theoretical or empirical deflection angle distributions of preforms, whose refractive index distribution is known. During measurement, the preform is positioned in a bath containing immersion liquid so as to prevent the deflection angle from becoming too large.

U.S. Pat. No. 4,441,811 describes a method and an apparatus for determining the refractive index distribution of a cylindrical, transparent optical preform. In this case, too, the preform which is inserted in immersion liquid is scanned by a transversely entering light beam that extends perpendicular to the optical axis. The light beam is deflected by the glass of the preform and imaged with an optical device onto a positionable detector. The refractive index profile is calculated from the deflection angle distribution by way of numerical integration. Other preform parameters, such as preform diameter, core diameter, eccentricity and CCDR value (cladding to core diameter ratio) can also be determined therefrom.

Methods for the reconstruction of the refractive index profile from the transversely measured deflection angle distribution by using the Abel transform can also be found in U.S. Pat. Nos. 4,744,654, 5,078,488 and 4,515,475. The two following technical articles also describe such methods: MICHAEL R. HUTSEL AND THOMAS K. GAYLORD "Concurrent three-dimensional characterization of the refractive-index and residual-stress distributions in optical fibers", APPLIED OPTICS, OPTICAL SOCIETY OF AMERICA, WASHINGTON, DC; US, Vol. 51, No. 22, 1 Aug. 2012 (Aug. 1, 2012), pages 5442-5452 (ISSN: 0003-6935, DOI: 10.1364/A0.51.005442) and FLEMING S. ET AL: "Nondestructive Measurement for Arbitrary RIP Distribution of Optical Fiber Preforms", JOURNAL OF LIGHTWAVE TECHNOLOGY, IEEE SERVICE CENTER, NEW YORK, N.Y., US, Vol. 22, No. 2, 1 Feb. 2004 (Feb. 1, 2004), pages 478-486 (ISSN: 0733-8724, DOI: 10.1109/JLT.2004.824464).

The simple reconstruction of the refractive index profile n(r) from the transversely measured deflection angle distribution using the Abel transform according to above equation (2) does not, however, lead to negligible differences with respect to the real refractive-index profile. The reason for this is a known measurement artifact that occurs in refractive index discontinuities on boundaries between the transparent object and the environment or on the boundary between radial refractive-index steps. As shall be explained in more detail with reference to FIG. 2, measurements taken on the boundaries of refractive index jumps from a low to a high refractive index (when viewed from the outside to the inside) in a near-boundary volume region of the optical object lead to a region that can in principle not be measured. Typical differences and errors of the reconstructed refractive-index profile, for instance, of step index profiles are roundings of the profile and step heights that are too small. The technical article by Werner J. Glantschnig with the title: "Index profile reconstruction of fiber preforms from data containing a surface refraction component"; Applied Optics 29 (1990), July, No. 19, 2899-2907, deals with the problems posed by the non-measurable region. It is suggested that, by way of extrapolation based on the inner three measuring points of the deflection angle distribution directly before the discontinuity, the actually missing deflection angles are so to speak filled up in the non-measureable region.

The extrapolation based on three measuring points does not, however, produce good results in every case. To solve this problem, U.S. Pat. No. 8,013,985 B2 suggests a modification of this reconstruction method in that, for the measurement of the refractive index profile of a transparent cylindrical object such as a fiber preform, a beam deflection angle function is measured and the refractive index profile is reconstructed from the measured data on the basis of the paraxial ray theory mathematically and by application of an inverse Abel transform to the deflection function. In the measurement, the fiber preform to be measured is arranged between a laser and a transform lens. The preform has a central axis and a cylinder surface that define a preform radius R. The entry beam impinging on the cylinder surface at height x is deflected in the preform and exits again as an exit beam at another angle, which is detected by means of a photodetector and processed by a controller. The deflection angle is defined as the angle between the exit beam and the entry beam and is changed by varying the laser beam height x, and the deflection angle distribution ii is measured. An estimated refractive-index profile that is representative of the real refractive-index profile is adapted by means of a numerical model to the measured deflection angle distribution.

To this end, a symmetry correlation is carried out on the measured deflection function to define a center coordinate. The measured deflection function is split into two halves about the center coordinate, and a refractive index half-profile is calculated for each of the two halves to obtain a resulting estimated index profile for each half. The relevant parameters for the refractive index profile calculation are the preform radius R and the refractive index of the preform. A target angle distribution $\psi_t$ is iteratively adapted to the measured deflection function, with measurement points close to a boundary (refractive index discontinuity) being omitted within or on the edge of the preform. This method of the arithmetical iterative adaptation of mathematical functions will also be called "fitting" in the following.

According to U.S. Pat. No. 8,013,985, fitting is conducted in that the above equation (1) (however without consideration of the arccos portion indicated in the second line of the equation) has inserted thereinto yet unknown parameters of the refractive index profile, namely a value for the preform radius R (or for the radius of the refractive index discontinuity), as well as yet unknown refractive index values $\eta_i$, wherein the yet unknown parameters are varied such that the target angle distribution $\psi_t$ obtained thereby best matches the measured deflection angle distribution $\psi_m$. The target angle distribution $\psi_t$ is thus adapted (fitted) with the yet unknown parameters R and $\eta_i$ to the measured deflection angle distribution $\psi_m$.

On the basis of the thus adapted, simulated target angle distribution $\psi_t$, a reconstructed refractive index profile $\eta^*_i(r)$ is calculated. This profile extends up to the reconstructed preform radius R* which is greater than the radius $R_{FIT}$ of the inner object region. For cylindrical objects whose refractive index profile has at least one discontinuity, the method is applied to the various object regions which are respectively defined by the discontinuity.

In this method, a simulated target angle distribution $\psi_t$ is adapted to the measured deflection angle distribution $\psi_m$ by fitting yet unknown parameters, and a radial refractive index distribution which can extend up to the boundary of a further externally located discontinuity of the refractive index profile is calculated from the simulated target angle distribution.

The detection of a complete refractive-index profile of an optical object having several layers radially separated by a refractive index discontinuity therefore requires a successive measurement, calculation and estimation of the layers defined by the respective discontinuity from the outside to the inside. Systematic and numerical errors may result in both the fitting of the simulated target angle distribution $\psi_t$ and in the conversion thereof into the reconstructed refractive-index profile $\eta^*_i(r)$.

Moreover, it has been found that the comparison of deflection angle distributions, namely a simulated one and a measured one, is not very illustrative and requires a high degree of expertise for determining whether and optionally how a fitting is optimal, or whether and optionally which value requires a post-correction or further variation.

It is therefore an objective of the present invention to provide a method for determining the refractive index profile of a cylindrical transparent object with a radially symmetric or approximately radially symmetric refractive-index distribution, which is improved in terms of plausibility, accuracy and reproducibility.

BRIEF SUMMARY OF THE INVENTION

In one embodiment, the present invention relates to a model comprising the following measures:
(a) preparing the measured deflection angle distribution $\Psi(y)$, including an extreme value determination of the deflection angle distribution, wherein a prepared deflection angle distribution $\Psi'(y)$ is obtained,
(b) transforming the prepared deflection angle distribution $\Psi'(y)$ into a prepared refractive-index profile n'(r),
(c) evaluating the prepared refractive-index profile n'(r) for the fixation of orientation values, comprising an orientation value $r^*_k$ for the layer radius and an orientation value $n^*_k$ for the layer refractive index of a hypothetical refractive index profile n*(r),
(d) generating a simulated deflection angle distribution $\Psi''(y)$ on the basis of the hypothetical refractive-index profile n*(r) with the orientation values $r^*_k$ and $n^*_k$, and transforming the deflection angle distribution into a simulated refractive-index profile n"(r), (e) fitting the simulated refractive index profile n"(r) to the prepared refractive-index profile n'(r) by iterative adaptation of the parameters $r^*_k$ and $n^*_k$, wherein a fitted, simulated refractive-index profile $n^*(r)_{fit}$ is obtained, which is defined by adapted parameters $r^*_{k,fit}$ and $n^*_{k,fit}$, and (f) obtaining the refractive index profile as the hypothetical refractive-index profile with the adapted parameters $r^*_{k,fit}$ and $n^*_{k,fit}$.

The deflection angle distribution Ψ(y) is normally determined by way of a so-called preform analyzer. The preform is here inserted into a measurement cell with an immersion liquid and the deflection angle distribution is measured.

In contrast to the prior art, which prompts the skilled person to apply the "Abel transform", the present invention teaches a modification of the method using above method steps (e) to (f). The method steps of the present invention define an iterative fitting of a simulated refractive index profile (n"(r)) to a second refractive index profile (n'(r)).

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
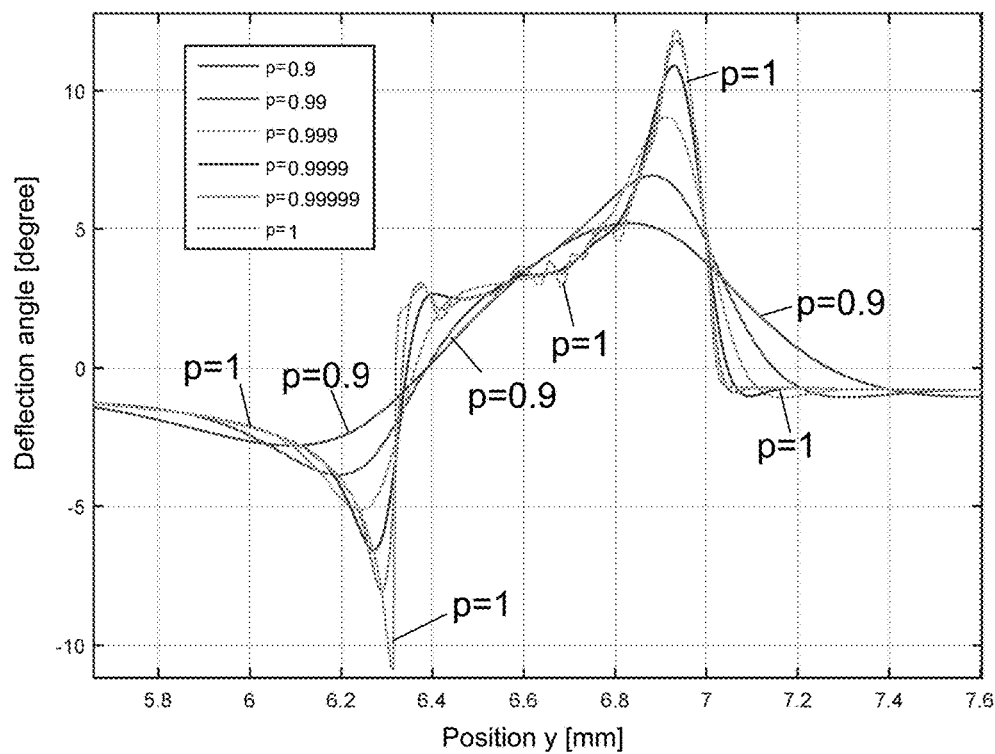
FIG. 1 shows a section of a measured deflection angle function with associated spline functions for various smoothing parameters p.

The method according to the invention serves to determine a refractive index profile of a cylindrical optical object, such as for instance an optical preform. The refractive index profile of a preform cannot be measured directly and is therefore indirectly determined as a deflection of a light beam transmitted through a volume region of the preform. The refractive index distribution of the preform can be deduced from the deflection of the exiting light beam.

Prepared Deflection Angle Distribution Ψ'(y)

In the method according to an embodiment of the present invention, a prepared deflection angle distribution Ψ'(y) is produced in a first step from the deflection angle distribution Ψ(y) measured in this way. For this purpose, the measured deflection angle distribution Ψ(y) is subjected to an analysis and determination of extreme values. Such extreme values occur, for instance, in the region of a refractive index jump, for instance on an inner boundary or on the cylinder surface of the optical object. For the sake of simplicity, the following explanations will refer to an optical preform with step index profile that comprises at least two layers and thus one or more refractive index jumps of that nature, inter alia the cylinder surface of the preform.

The deflection angle distribution of radially symmetric objects has at least two extreme values that are caused by the refractive index jump on one and the same layer k. In the determination of the extreme values, the positions of the extreme values $y_{k,max}$ of the measured deflection angle distribution are determined. The positions are already approximately the edges on both sides (numerically defined by the radius of the corresponding layer) where the refractive index jump occurs. This determination of the extreme values shall also be called "edge detection" in the following.

Attention must be paid that the measurement data of the deflection angle distribution refer to a Cartesian coordinate system, and are here indicated dependent on the y-axis thereof, whereas the radii of the layers normally refer to a different coordinate system (radial system) and are indicated dependent on the radius r. In the case of small refractive-index differences and a weak refraction, the difference may be so small that a distinction is often not made between y- and r-values, which is called "approximation method", "straight-line approximation" or "no-refraction-approximation" in the literature.

In edge detection, it shall be avoided as much as possible that an edge is erroneously assumed because of outliers or measurement noise. It has been found that a procedure in which the measured deflection angle distribution is smoothed by way of spline functions using several different smoothing parameters is particularly well suited for this. The spline functions are several composed polynomials of a higher order. By iterative application of weaker smoothing parameters, the respective extrema are gradually shifting in each iteration towards the actual extrema.

Thus, in edge detection, an innermost right extreme value $y_{k,right}$ and an innermost left extreme value $y_{k,left}$ are preferably determined. As discussed above, these values approximately correspond to the corresponding edges of the k-th layer of the refractive index profile. This is, for instance, the outer edge of the core or the outer edge of a cladding layer (but with the proviso that the refractive indices are increasing from the outside to the inside, so that no total reflection occurs because the corresponding edge would possibly lie in a de facto non-measureable region). The right and left edges determined in this way are particularly well suited to define the actual center point of the preform.

Moreover, the preparation of the measured deflection angle distribution preferably comprises a correction in which the origin of the deflection angle distribution is adjusted.

The coordinate origin of the deflection angle distribution in the Cartesian coordinate system through which (at y=0) the cylinder longitudinal axis of the preform is to extend is here called origin. A shift along the y-axis may occur because, in the measurement of the deflection angle distribution by way of a preform analyzer, the y-axis is solely defined through the geometry of the measurement cell.

The center of the measurement cell, however, does not automatically correspond to the longitudinal axis of the preform.

Therefore, the adjustment of the origin of the deflection angle distribution comprises, for instance, a shift in the direction of the y-axis of the coordinate system into the middle between innermost right extreme value $y_{k,right}$ and innermost left extreme value $y_{k,left}$.

Moreover, the whole angle distribution may comprise an offset from the coordinate origin in the form of a shift in the direction of the vertical axis (this is the $\Psi$-axis in the coordinate system of the deflection angle distribution). The determination of an offset is preferably carried out in that a distance is determined between the zero line (y=0) of the coordinate system and a straight line which is fitted by way of a sum of least squares method to the middle between innermost right extreme value $y_{k,right}$ and innermost left extreme value $y_{k,left}$ of the refractive index profile. For the elimination of the offset, the deflection angle distribution is shifted by the distance determined in this way in the direction of a $\Psi$ axis of the coordinate system.

For the fitting of the straight line, it is not the entire route between the edges that has to be taken into account, but a shorter sub-route is preferably used that is less than 20% of the total route.

In an alternative, equally preferred process variant for determining the offset, a higher-order polynomial (e.g., of the $9^{th}$ order) is fitted to the middle between innermost right extreme value $y_{k,right}$ and innermost left extreme value $y_{k,left}$. A sub-route between the edges or the entire route can here also be chosen.

In a further alternative, and also preferred process variant for determining the offset, the deflection angle distribution is shifted such that the sum of all equidistantly measured deflection angles is equal to zero.

The outcome of the evaluation and preparation is a prepared deflection angle distribution $\Psi'(y)$ which is adapted with respect to its origin to the coordinate origin.

Prepared Refractive Index Profile n'(r)

In a next step, a refractive index profile which is here called "prepared refractive index profile n'(r)" is produced from the prepared deflection angle distribution $\Psi'(y)$ by transformation. The generation of a refractive index profile from the originally measured deflection angle distribution is not required for this.

It has been found that the previous adaptation of the origin of the deflection angle distribution is of great help to this transformation which is e.g. conducted by way of an Abel transform, for instance the above equation (2). Without an adaptation, already small deviations from the actual origin lead to errors in the transformed refractive-index distribution.

The prepared refractive-index profile n'(r) is still without refractive-index and radius values from the "non-measurable region," so that it does not reflect the refractive index profile of the preform which is to be expected in reality. However, it represents an illustrative orientation guide from which suitable orientation values for a "hypothetical refractive index profile" n*(r), which is the basis for the subsequent process step, can be derived in a relatively unambiguous manner. The orientation values to be derived comprise an orientation value r*k for the layer radius and an orientation value n*k for the layer refractive index of the hypothetical refractive index profile n*(r). Empirical values and data stored in databases, which can additionally be used for determining the refractive index, often exist especially for the refractive index.

In the simplest case, the determined extreme values $y_{k,right}$ and $y_{k,left}$ are used for the fixation of the orientation value r*k in the evaluation of the prepared refractive-index profile n'(r) according to measure (c).

However, as has been explained above in connection with the approximation method, this is only approximately correct. In a particularly preferred process variant, the determined extreme values $y_{k,right}$ and $y_{k,left}$ are therefore converted into layer radii $r_{k,right}$ and $r_{k,left}$, respectively, and the calculated layer radii are used for the fixation of the orientation value r*k.

The conversion of the extreme values in the layer radius is here preferably carried out on the basis of one of the following equations (3) and (4):

$$r^*_k = n_0/n_{k-1} * y_{k,max} \quad (3)$$

$$r^*_k = n_0/n_k * y_{k,max} \quad (4)$$

where: $n_0$=refractive index of the surrounding medium,
$n_{k-1}$=refractive index of the layer adjoining layer k on the outside
$n_k$=refractive index of layer k
$y_{k,max}$=position of the deflection angle of layer k with the maximum absolute value.

Equation (3) is applicable in cases where no total reflection takes place on the boundary at $r_k$. Otherwise, equation (4) is applicable.

The hypothetical refractive-index profile is based on the prepared refractive-index profile n'(r) and the orientation values derived from this profile, which, in turn, include estimate values for refractive index and radii from the "non-measurable region". It already depicts the refractive index profile of the preform to be expected in reality, or it is close to this refractive index profile.

Simulated Refractive-Index Profile n"(r)

A simulated deflection angle distribution $\Psi''(y)$ is produced from the hypothetical refractive-index profile n*(r) in the next method step. The above-mentioned equation (1) is for instance suited for this conversion. The simulated deflection angle distribution $\Psi^*(y)$ is thus based on the assumption of a refractive index profile of the preform (namely the hypothetical refractive index profile n*(r)) which in turn is derived from a prepared refractive index profile n'(r) after correction and evaluation of original measurement values.

A simulated refractive-index profile n"(r) is again obtained by transformation of the simulated deflection angle distribution $\Psi'''$ (y), for instance, on the basis of the above equation (2).

Hence, a simulated refractive-index profile n"(r) is obtained by simulation via the auxiliary construct of the hypothetical refractive-index profile n*(r) from the prepared refractive-index profile n'(r). The more the simulated refractive-index profile n"(r) resembles the prepared refractive-index profile n'(r), the closer are the assumptions underlying the hypothetical refractive-index profile n*(r) to reality, i.e. the real refractive-index profile n(r) of the preform.

Real, Reconstructed Refractive-Index Profile n(r)

Ideally, if simulated refractive-index profile n"(r) and prepared refractive-index profile n'(r) are a match, the hypothetical refractive-index profile n*(r) underlying the simulation would thus reflect the real refractive-index profile of the preform.

In practice, an exact match is not achievable. An adequate and arbitrarily accurate adaptation is however achievable by iterative fitting of the simulated refractive-index profile n"(r) to the prepared refractive-index profile n'(r). The iteration includes at least one run of the simulation according to method step (d). The outcome is a sufficiently accurate, fitted, simulated refractive-index profile $n''(r)_{fit}$ that is defined by parameters $r^*_{k,fit}$ and $n^*_{k,fit}$ which are adapted in an optimal or adequate way. Thus, the hypothetical refractive-index profile underlying this very simulation with the adapted parameters $r^*_{k,fit}$ and $n^*_{k,fit}$ simultaneously represents the reconstructed, real refractive-index profile of the preform.

As a mathematical criterion whether a sufficiently fitted, simulated refractive-index profile $n^*(r)_{fit}$ is present, one can calculate whether the deviation between simulated refractive-index profile $n''(r)$ and prepared refractive-index profile $n'(r)$ is below a given threshold value. The calculation of the deviation is preferably carried out on the basis of the "least absolute residuals" or on the basis of the "least squares method". In the case of equidistant radii, the absolute residuals correspond to so-called "best-fit areas".

Since, according to embodiments of the present invention, the finding of the optimized parameters $r^*_{k,fit}$ and $n^*_{k,fit}$ as well as the finding of sufficiently adapted (fitted) profiles is based on refractive index profiles, and not on the level of deflection angle distributions, simplifications and improvements are achieved with respect to plausibility, accuracy and reproducibility of the measurement results.

Ideally, every layer of the optical objet shows the given layer refractive index $n_k$ over the whole layer radius rk. In reality, however, there are deviations from this. The layer refractive index $n_k$ may vary around the nominal value and its evolution may differ from the constant value. The reconstruction of the refractive-index profile on the basis of the method according to embodiments of the present invention does not presuppose an ideal step profile. Deviations are leveled to a mean value of the real layer refractive index. This is equally applicable to a layer with preset refractive-index gradient.

In a particularly preferred embodiment of the method according to the present invention, a fitting of the simulated deflection angle distribution $\Psi^*(y)$ to the prepared deflection angle distribution $\Psi''(y)$ is carried out by iterative adaptation of the parameters $r^*_k$ and $n^*_k$ according to measure (d) in addition to the fitting of the simulated refractive index profile $n''(r)$ to the prepared refractive-index profile $n'(r)$ according to method step (e), wherein a fitted, simulated deflection angle distribution $\Psi''^*(y)_{fit}$ is obtained that is defined by adapted parameters $r'^*_{k,fit}$ and $n'^*_{k,fit}$, and wherein the refractive index profile is obtained according to method step (f) by the measure that the fitted, simulated refractive-index profile $n^*(r)_{fit}$ with a weighting factor G is combined with the fitted, simulated deflection angle distribution $\Psi''^*(y)_{fit}$ with a weighting factor $(1-G)$, where $0<G<1$.

To reconstruct the real refractive-index profile $n(r)$, weighted parameters are here used that are obtained by viewing the refractive index plane from the fitted, simulated refractive-index profile $n''(r)_{fit}$ on the one hand, and by viewing the angle plane due to the fitted, simulated deflection angle distribution $\Psi''^*(y)_{fit}$ on the other hand. Random measurement value variations or conversion errors are thereby eliminated in addition, whereby a higher accuracy is achieved in the reconstruction of the real refractive-index profile.

The parameters determined on the basis of the reconstruction of the real refractive-index profile $n(r)$, particularly the adapted parameters $r^*_{k,fit}$ and $n^*_{k,fit}$, are preferably used for the adaptation of a preform manufacturing process.

The method according to an embodiment of the present invention serves to determine a refractive index profile of a cylindrical optical object, such as, for instance, an optical preform. The refractive index profile of a preform cannot be measured directly, and is therefore indirectly determined as a deflection of a light beam transmitted through a volume region of the preform. The refractive index distribution of the preform can be deduced from the deflection of the exiting light beam.

The measurement of the deflection angle distributions is carried out by way of a commercially available P-102 preform analyzer of the company York Technology Ltd. The standard operating wavelength of the device is 632.8 nm, but other wavelengths may also be used. The device determines the deflection angle distribution mainly automatically on the basis of the so-called dynamic spatial filtering technique. The collimated light is here refracted by the preform, leaving the preform at a deflection angle $\psi$. A spherical lens which images every ray with deflection angle $\psi$ onto a point in a focal plane is positioned behind the preform. A rotating disc with a recess in the form of a circular sector is there positioned at a distance R under the optical axis. The preform is mounted in a measurement cell filled with immersion oil, which can be moved by means of a step motor in y-direction (perpendicular to the main propagation direction x of the measurement beam and perpendicular to the height direction z). In the imaging plane, a photodiode is positioned as a detector. The recess of the rotating disc acts like a blade which can be passed through by those beams that have an adequate refraction (deflection) and that produce the spatial distribution of the deflection angle in the imaging plane. The P-102 preform analyzer carries out all necessary calculations automatically, so that the data array of the deflection angle distribution $\Psi(y)$ can be directly plotted, output and stored.

The diagram of FIG. 1 shows a section of a typical deflection angle function measured in this way, using the example of a preform in which a core rod of undoped quartz glass is surrounded by an inner cladding layer of fluorine-doped quartz glass and an outer cladding layer of quartz glass that is undoped again. The deflection angle $\Psi$ (in degrees) is plotted versus the position along the y-axis (in mm). The curve designated by "p=1" corresponds to the measurement curve. In the diagram, several spline functions for various smoothing parameters p<1 are also plotted. These demonstrate the effect of the various smoothing steps and will be explained in more detail further below.

Figure 2:
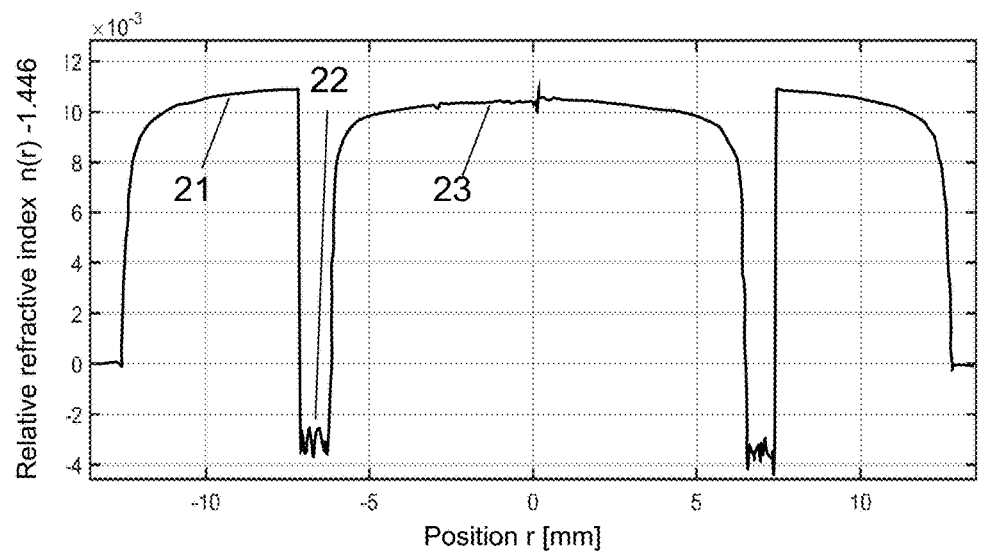
FIG. 2 shows a refractive index distribution, calculated from the measured deflection angle distribution (p=1) of FIG. 1.

The calculation of the refractive index distribution $n(r)$ from the deflection angle distribution is carried out by way of an Abel transform (above equation 2). In the corresponding diagram of FIG. 2, the relative refractive index $n-n_0$ is plotted versus the radius r (in m). The curve which is only shown by way of example was calculated from the measured deflection angle distribution (p=1) of FIG. 1 by way of numerical integration. The curve in region 21 represents the core rod, the curve in region 22 the inner cladding layer, and the curve in region 23 the outer cladding layer.

Figure 3:
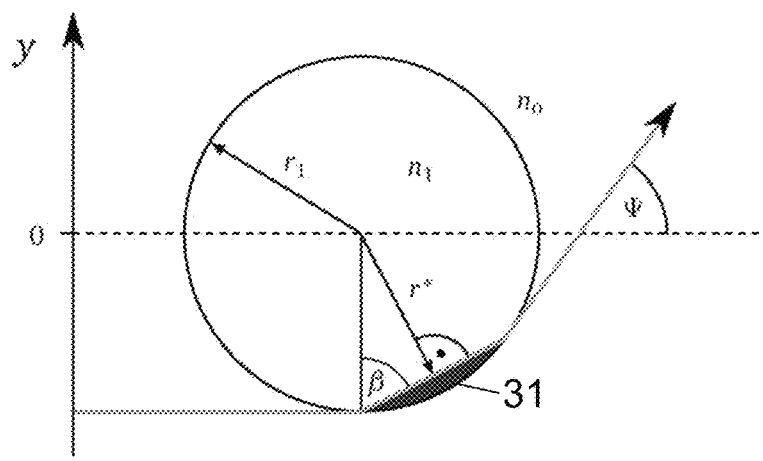
FIG. 3 shows the radiation path with maximum minimal radius r* through a rod with homogeneous refractive index distribution for illustrating the non-measurable region.

These measurement results are, however, not correct. One of the reasons for this is the occurrence of a non-measurable region caused by the measuring method in the case of an upward refractive-index jump, as is typical of optical fibers with a comparatively higher refractive index in the core than in the inner cladding layer. The reason for the error is illustrated in the sketch of FIG. 3 by reference to a simple case, namely a rod with homogeneous refractive-index distribution $n_1$, which is inserted into an index adaptation liquid (immersion liquid) with refractive number $n_0$, where $n_0$ is less than $n_1$. During scanning of the rod, the beam 32 which impinges tangentially at the entry point E is refracted towards the center of the rod and exits again as an exit beam 22 with a different propagation direction from the rod, resulting in a beam path as shown in FIG. 3. Thus, there is a region 31 through which no light beam can be transmitted tangentially in this measurement. As a consequence, it is not possible to measure deflection angles in the region r*<r<r1, and it becomes apparent that due to this the reconstructed refractive-index value is lower than the real refractive index.

The aim of the procedure explained hereinafter with an evaluation and modeling of the measured deflection angle distribution is a compensation of this systematic measurement error and a substantial reconstruction of the real refractive-index profile n(r).

Evaluation and Preparation of the Measured Deflection Angle Distribution

At the beginning of the evaluation, the positions of the extrema $y_{k,max}$ of the measured deflection angle distribution are determined. These are already approximately the radii of the individual layers. In principle, the exact positions on the positive and negative y-axis of the core rod edge can be determined by simple manual reading, particularly in the case of ideal data without noise.

An embodiment of the method according to the present invention shall be explained hereinafter with reference to FIG. 1. The measurement data used for this correspond to curve "p=1. To ensure that the edge is not erroneously placed on outlying measurement points or secondary extrema caused by noise, the measured deflection angle distribution is strongly smoothed by way of spline functions at the beginning.

The spline functions are several composed higher-order polynomials, e.g. of the third order. The smoothing parameters "p" represent for instance a compromise between:
p=1: section-wise fit of cubic polynomials
0<p<1: section-wise fit of a smoothed curve
p=0: fit of a straight line.

One starts with p=0.9, i.e. a strong smoothing. The deflection angle increases in its absolute value over a wide region from the inside to the outside, towards an edge. The strongly smoothed deflection angle curve shows a maximum or minimum in this region, depending on the sign of the deflection angle. A few outlier data points yield, if at all, small extrema only. The extreme values are determined on the strongly smoothed curve. Subsequently, a smoothing with p=0.99 (less smoothing) takes place. This step is repeated for p=0.999; p=0.9999; p=0.99999 and finally for the original measurement data (p=1), with a gradually decreasing smoothing. There is no longer any smoothing in the sixth and last iteration (p=1). It is true that the selection of p=1 corresponds to the cubic interpolation, but if it is evaluated especially at the support points, the original points are in fact obtained again. Hence, the curve p=1 represents a section of the measured data.

Thus, the extreme values determined previously on the basis of the strong smoothing shift gradually with every iteration towards the actual extrema of the deflection angle distribution and thus tend to move also towards the real refractive-index edge. The real position of the refractive index edge is thus optimally approximated by the highest smoothing parameter. The real edge position is in the case of a downward refractive-index jump at the bottom of the maximum and, vice versa, in the case of an upward refractive-index jump at the peak of the maximum.

The innermost extrema $y_{k,right}$ and $y_{k,left}$ of the deflection angle distribution which have been found by way of this evaluation are used in the further evaluation. They particularly serve the correction of the origin of the deflection angle distribution. Subsequently, the original deflection angle distribution is once again smoothed by way of spline functions, but this time less strongly at p=0.99.

Before the transformation by way of equation (2) is carried out, the origin of the deflection angle distribution Ψ(y) is correctly determined. Specifically, the y-axis in the coordinate system of the angle distribution is only determined through the geometry of the measurement cell. Here, the center of the measurement cell does not necessarily have to conform to that of the preform, which leads to a shift towards the y-axis. Moreover, the whole angle distribution may have an angle offset with a shift contribution in z-direction of this coordinate system. This can, for instance, be caused by an inaccurate referencing of the angle of the rotating disc in the measurement device.

Figure 4:
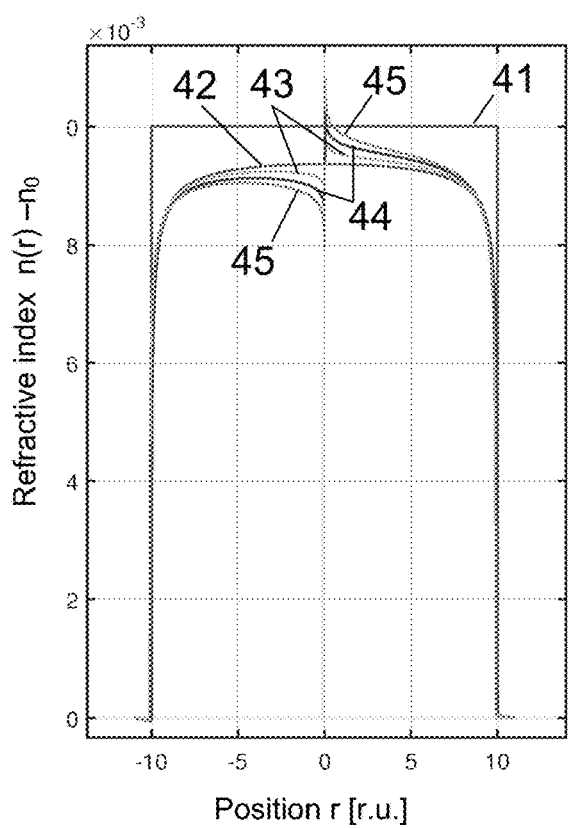
FIG. 4 shows diagrams with different refractive-index distributions for illustrating the impact of an offset in the origin of the underlying deflection angle distributions.

FIG. 4 shows the impacts of an offset in the origin of the underlying deflection angle distributions on the refractive index distribution calculated therefrom. To this end, two distributions consisting of 4401 data points were made by means of equation (1) and the calculation was subsequently carried out. Profile 41 is the assumed step profile with a refractive index jump Δn=±0.01. The remaining curves show calculations of the refractive index profile, plotted as refractive index difference $(n(r)-n_0)$ versus the position r in relative units (r.u.):

Curve 42: from a correct deflection angle distribution
Curve 43: an incorrect positioning of the origin in y-direction of 0.1 mm
Curve 44: an incorrect positioning of the origin with an angle offset of −0.02° (~$3.5 \cdot 10^{-4}$ rad)
Curve 45 with both shifts together.

Curve 42 shows the consequences of a typical systematic error in the conversion of a measured deflection angle distribution in refractive index profiles. The total refractive-index level is clearly lower than the real level. Moreover, there is a rounding off of the refractive index profile towards the edge. Curves 43 to 45 show the impacts of the incorrect positioning of the origin.

Optical preforms are substantially radially symmetric, so that the previously determined core rod edges in the deflection angle distribution are particularly well suited for the determination of the preform center point and thus the coordinate origin. If necessary, the y-axis is shifted by the corresponding path, so that the origin lies exactly in the middle between the core rod edges.

The correction of the offset is conducted in order to vertically shift the deflection angle distribution accordingly. To this end, a straight line is fitted by way of a sum of least squares method to the middle between innermost right extreme value $y_{k,right}$ and innermost left extreme value $y_{k,left}$. The region to be fitted extends over not more than 20% of the core rod diameter. The measurement data are finally shifted vertically around the y-axis section of the straight line, so that the straight line runs through the origin.

In an alternative process variant for determining the offset, a higher-order polynomial (for instance $9^{th}$ order) is fitted to the middle between innermost right extreme value $y_{k,right}$ and innermost left extreme value $y_{k,left}$. Here, a sub-route between the edges or the entire route can also be chosen. In a further alternative process variant for determining the offset, the deflection angle distribution is shifted such that the sum of all equidistantly measured deflection angles is equal to zero.

The result of the evaluation and preparation is a prepared deflection angle distribution Ψ'(y) which is adapted with respect to its origin to the coordinate origin.

In a next step, a prepared refractive-index profile n'(r) is produced from the prepared deflection angle distribution Ψ'(y) by way of the Abel transform according to the above equation (2). As illustrated with reference to FIG. 4, the previous adaptation of the origin of the deflection angle distribution is here very helpful, for without this already small deviations from the actual origin would lead to errors in the transformed refractive index distribution.

It is true that the prepared refractive index profile n'(r) does not reflect the refractive index profile of the preform that is really to be expected. However, it represents an illustrative orientation guide from which suitable orientation values for a "hypothetical refractive index profile" n*(r) can be derived in a relatively definite way, the hypothetical refractive index profile forming the basis for the subsequent method step. The orientation values to be derived comprise an orientation value r*k for the layer radius and an orientation value n*k for the layer refractive index of the hypothetical refractive index profile n*(r). Especially for the refractive index, there are often empirical values and data stored in databases which can additionally be used for determining the refractive index.

In this evaluation, the previously determined extreme values $y_{k,right}$ and $y_{k,left}$ are also used for determining the orientation value r*k. However, since these positions correspond only approximately to the radii of the refractive index profile, the determined extreme values $y_{k,right}$ and $y_{k,left}$ are converted to layer radii $r_{k,right}$ and $r_{k,left}$, respectively, and the calculated layer radii are used for fixing the orientation value r*k. The conversion of the extreme values into the layer radius takes place on the basis of equation (3) in the event that no total reflection takes place on the boundary at $r_k$, and it takes place on the basis of equation (4) in the event that a total reflection does take place on the boundary at $r_k$.

Figure 5:
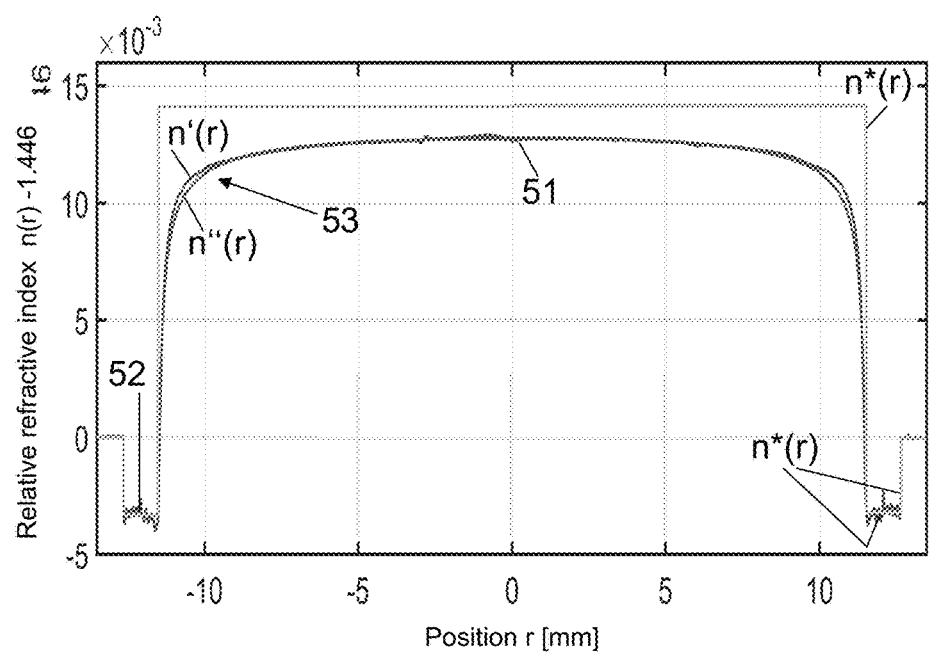
FIG. 5 shows a diagram with a prepared refractive index profile n'(r) and a hypothetical refractive index profile n*(r) modeled by evaluation of said profile for a preform with step profile.

The diagram of FIG. 5 shows, for a preform with a simple step profile, a prepared refractive-index profile n'(r) and a hypothetical refractive-index profile n*(r) modeled by evaluation thereof. The refractive index is indicated as a relative value based on the refractive index of the index adaptation liquid ($n_0$=1.446).

The hypothetical refractive-index profile n*(r) already depicts the refractive index profile of the preform to be expected in reality, or it is close to the refractive index profile. It is based on the prepared refractive-index profile n'(r) and the orientation values derived from the profile, which, in turn, include estimation values for refractive index and radii from the "non-measurable region".

By conversion with equation (1), a simulated deflection angle distribution Ψ''(y) is produced from the hypothetical refractive-index profile n*(r) in the next method step. The simulated deflection angle distribution Ψ*(y) obtained thereby is thus based on the assumption of a refractive index profile of the preform (namely the hypothetical refractive-index profile n*(r)), which, in turn, after correction and evaluation of original measurement values, is derived from a prepared refractive-index profile n'(r).

A simulated refractive-index profile n''(r), plotted with this designation in FIG. 5, is obtained again by transforming the simulated deflection angle distribution Ψ''(y) on the basis of the above equation (2). The profile has a rounded region 53 between cladding region 52 and core region 51. Apart from this rounded region 53, the simulated refractive-index n''(r) is almost congruent with the prepared refractive-index profile n'(r). Considering that the assumed refractive-index distribution n*(r) considerably differs therefrom, this is remarkable. The similarity is a hint that the assumptions underlying the hypothetical refractive-index profile n*(r) are already very close to the real refractive-index profile n(r) of the preform. That is, the hypothetical refractive-index profile n*(r) in FIG. 5 reflects the real refractive-index profile n(r) accurately or at least adequately accurately.

In practice, an exact match between simulated refractive-index profile n''(r) and prepared refractive-index profile n'(r) is not achievable. However, it is possible to achieve an adequately and arbitrarily accurate adaptation by iteratively fitting the simulated refractive-index profile n''(r) to the prepared refractive-index profile n'(r).

During iterative fitting, the parameters $r*_k$ and $n*_k$ are varied for such a long time that an adequately accurate, fitted, simulated refractive-index profile $n''(r)_{fit}$ is obtained. The parameters $r*_{k,fit}$ and $n*_{k,fit}$ used therein form the basis for the corresponding hypothetical refractive-index profile n*(r) which with these parameters thereby represents the reconstructed, real refractive-index profile of the preform at the same time.

A criterion whether an adequately fitted, simulated refractive-index profile $n*(r)_{fit}$ is present is the minimum in the deviation between the simulated refractive-index profile n''(r) and the prepared refractive-index profile n'(r), which is, for example, determined on the basis of the "sum of the least absolute residuals."

Even in the case of a rather complex refractive-index profile of a preform with eight layers, the measurement method according to the present invention yields a good result. The fitting of the layer parameter preferably takes place starting from the outer layer to the inside.

In the above-explained model for the reconstruction of the real refractive index profile of FIG. 5, simulated refractive-index profiles n''(r) were fitted to the prepared refractive-index profile n'(r). In a modification of this procedure for reconstruction, weighted parameters were additionally used that were obtained by considering the refractive index plane from the fitted, simulated refractive-index profile $n''(r)_{fit}$, on the one hand, and by considering the angular plane due to the fitted, simulated deflection angle distribution $Ψ'*(y)_{fit}$, on the other hand. This eliminates random measurement value variations or conversion errors in addition, and thereby achieves a higher accuracy in the reconstruction of the real refractive-index profile.

Here, simulated deflection angle distributions Ψ*(y) are additionally fitted to the prepared deflection angle distribution Ψ' (y). The fitting process is here based on the iterative adaptation of the parameters $r*_k$ and $n*_k$. The parameters are varied until a sufficiently accurate, fitted, simulated deflection angle distribution $Ψ''(r)_{fit}$ is obtained. The optimally adapted parameters $r'*_{k,fit}$ and $n'*_{k,fit}$, which are here used, form the basis for the corresponding hypothetical refractive-index profile n*(r), but they may differ from the optimally adapted parameter values $r*_{k,fit}$ and $n*_{k,fit}$. The information additionally gained thereby is additionally taken into account in the reconstruction of the refractive index profile by combining the fitted, simulated refractive index profile $n*(r)_{fit}$ with a weighting G=0.5 with the fitted, simulated deflection angle distribution $Ψ'*(y)_{fit}$ (also G=0.5).

To be able to determine the refractive indices $n_k$ and radii $r_k$ of the individual layers more accurately, a fit by way of the least squares method or the method of the least absolute residuals is advisable.

The greatest problem is that the fit function n(r) has no analytical expression. Therefore, a detour is taken for establishing the fit function. Within an iteration, the parameters $n_k$ and $r_k$ are varied each time, a deflection angle distribution is established therefrom by way of equation (1), transformation is carried out by way of equation (2) to finally compare the resulting profile n(r) by means of the least squares criterion or by means of the method of the least absolute residuals with the refractive index distribution of the measurement. The calculation of the transformation is therefore a fixed component of each iteration, which prolongs the computing time.

To be able to ensure a fitting within a shorter period of time, the following restrictions can be made:

Correction of the origin:
Due to the origin correction the offset in Ψ direction and the shift in y-direction, which would otherwise be independent fit parameters, are omitted. The number of independent fit parameters is thereby reduced by two.

Side-wise fitting:
To consider even minimal deviations within the preform with respect to the radial symmetry in the fit, various layer parameters $n_k$ and $r_k$ are allowed within a layer for the positive and negative y-axis. The fit, however, can be separated into two fits with only half the number of free fit parameters, which entails a considerable reduction of the required iterations and thereby saves time.

Layer-wise fitting:
Starting from the basic idea of splitting a fit with many free parameters into several fits with a few free parameters, layer-wise fitting is additionally possible, apart from sidewise fitting. However, it must here be taken into account that the parameters $n_k$ and $r_k$ which are to be determined must be determined from the outside to the inside. Hence, the number of the layers under consideration is thereby successively increased, and the considered region of the fit is also increasing layer-wise. Together with the previously explained sidewise fitting, one obtains in a preform with k layers 2·k fits with respectively 2 unknown parameters to be determined, instead of a fit with 4·k. The required computing time is thereby considerably reduced.

Reduction of the radii $r_k$ as free fit parameters:
According to the standard fit procedure the radii $r_k$ are free fit parameters. Alternatively, these can be parameterized by way of equations (3) and (4). $n_0$ is here the reference refractive index. The extreme values $y_{k,max}$ determined with the help of the above-explained method are fixed, so that the radii $r_k$ can only be changed with the variation of the refractive indices $n_k$. The required computing time can thereby be reduced into the range of seconds.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. Method for determining a radial refractive-index profile of a cylindrical optical object which has a cylinder longitudinal axis around which at least one layer k with a layer radius $r_k$ and with a layer refractive index $n_k$ extends radially symmetrically, the method comprising:

measuring a deflection angle distribution Ψ(y), measuring of the deflection angle distribution Ψ(y) comprising directing an entry beam at an entry point into the cylindrical optical object in a direction transverse to the cylinder longitudinal axis, wherein deflection angle Ψ is defined as the angle between an exit beam relative to the entry beam, and y is the distance between the cylinder longitudinal axis and the entry point of the entry beam in a Cartesian coordinate system; and reconstructing the refractive index profile therefrom on the basis of a model, the model comprising the following measures:

(a) adjusting the measured deflection angle distribution Ψ(y), including an extreme value determination of the deflection angle distribution and including regions of a refractive index step, wherein an adjusted deflection angle distribution Ψ'(y) is obtained and wherein the adjusting of the measured deflection angle distribution comprises a correction in which the origin of the deflection angle distribution is adjusted, (b) transforming the adjusted deflection angle distribution Ψ'(y) into an adjusted refractive-index profile n'(r), (c) evaluating the adjusted refractive-index profile n'(r) for fixation of orientation values, the orientation values comprising an orientation value $r^*_k$ for the layer radius and an orientation value $n^*_k$ for the layer refractive index of a hypothetical refractive-index profile n*(r), (d) creating a simulated refractive-index profile n"(r) by generating a simulated deflection angle distribution Ψ'''(y) on the basis of the hypothetical refractive-index profile n*(r) with the orientation values $r^*_k$ and $n^*_k$, and transforming said deflection angle distribution into the simulated refractive-index profile n"(r), (e) fitting the simulated refractive index profile n"(r) to the adjusted refractive-index profile n'(r) by iterative adaptation of the orientation values $r^*_k$ and $n^*_k$, wherein a fitted, simulated refractive-index profile $n^*(r)_{fit}$ is obtained which is defined by adapted parameters $r^*_{k,fit}$ and $n^*_{k,fit}$, and (f) obtaining the refractive index profile as the hypothetical refractive-index profile with the adapted parameters $r^*_{k,fit}$ and $n^*_{k,fit}$.

2. The method according to claim 1, wherein the extreme value determination according to measure (a) is a smoothing of the measured deflection angle distribution by means of a spline function using several different smoothing parameters.

3. The method according to claim 2, wherein in the extreme value determination, an innermost right extreme value $y_{k,right}$ and an innermost left extreme value $y_{k,left}$ are determined.

4. The method according to claim 3, wherein the preparation of the measured deflection angle distribution comprises a correction in which the origin of the deflection angle distribution is adjusted and wherein the adjustment of the origin of the deflection angle distribution comprises a shifting in the direction of a y-axis of the coordinate system into the middle between innermost right extreme value $y_{k,right}$ and innermost left extreme value $y_{k,left}$ of the refractive index profile.

5. The method according to claim 3, wherein in the evaluation of the adjusted refractive-index profile n'(r) according to measure (c), the determined extreme values $y_{k,right}$ and $y_{k,left}$ are used for the fixation of the orientation value $r^*_k$.

6. The method according to claim 5, wherein the adjustment of the origin of the deflection angle distribution comprises a shifting in the direction of a y-axis of the coordinate system into the middle between innermost right extreme value $y_{k,right}$ and innermost left extreme value $y_{k,left}$ of the refractive index profile.

7. The method according to claim 3, wherein the determined extreme values $y_{k,right}$ and $y_{k,left}$ are converted into layer radii $r_{k,right}$ and into $r_{k,left}$, respectively, and the layer radii are used for the fixation of the orientation value $r^*_k$.

8. The method according to claim 7, wherein the preparation of the measured deflection angle distribution comprises a correction in which the origin of the deflection angle distribution is adjusted and wherein the adjustment of the origin of the deflection angle distribution comprises a shifting in the direction of a y-axis of the coordinate system into the middle between innermost right extreme value $y_{k,right}$ and innermost left extreme value $y_{k,left}$ of the refractive index profile.

9. The method according to claim 3, wherein the preparation of the measured deflection angle distribution comprises a correction in which the origin of the deflection angle distribution is adjusted.

10. The method according to claim 9, wherein the adjustment of the origin of the deflection angle distribution comprises a shifting about an offset in the direction of a z-axis of the coordinate system, wherein the offset is calculated as a positional difference between the zero line of the coordinate system and a straight line which with the help of the sum of least squares method is fitted to the middle between innermost right extreme value $y_{k,right}$ and innermost left extreme value $y_{k,left}$.

11. The method according to claim 1, wherein the transformation of the prepared refractive-index profile n'(r) according to measure (b) is carried out on the basis of an Abel transform.

12. The method according to claim 1, wherein a fitted, simulated refractive-index profile $n^*(r)_{fit}$ is present when the deviation between the simulated refractive-index profile n"(r) and the adjusted refractive-index profile n'(r), as calculated on the basis of the "least absolute residuals" or on the basis of the "least squares method," is below a predetermined threshold value.

13. The method according to claim 1, wherein the parameters determined in the reconstruction of the real refractive-index profile n(r), in particular the adapted parameters $r^*_{k,fit}$ and $n^*_{k,fit}$, are used for the adaptation of a preform manufacturing process.

* * * * *